July 22, 1947. C. P. MALMO Plant Pat. 744
PENTSTEMON PLANT
Filed April 8, 1946
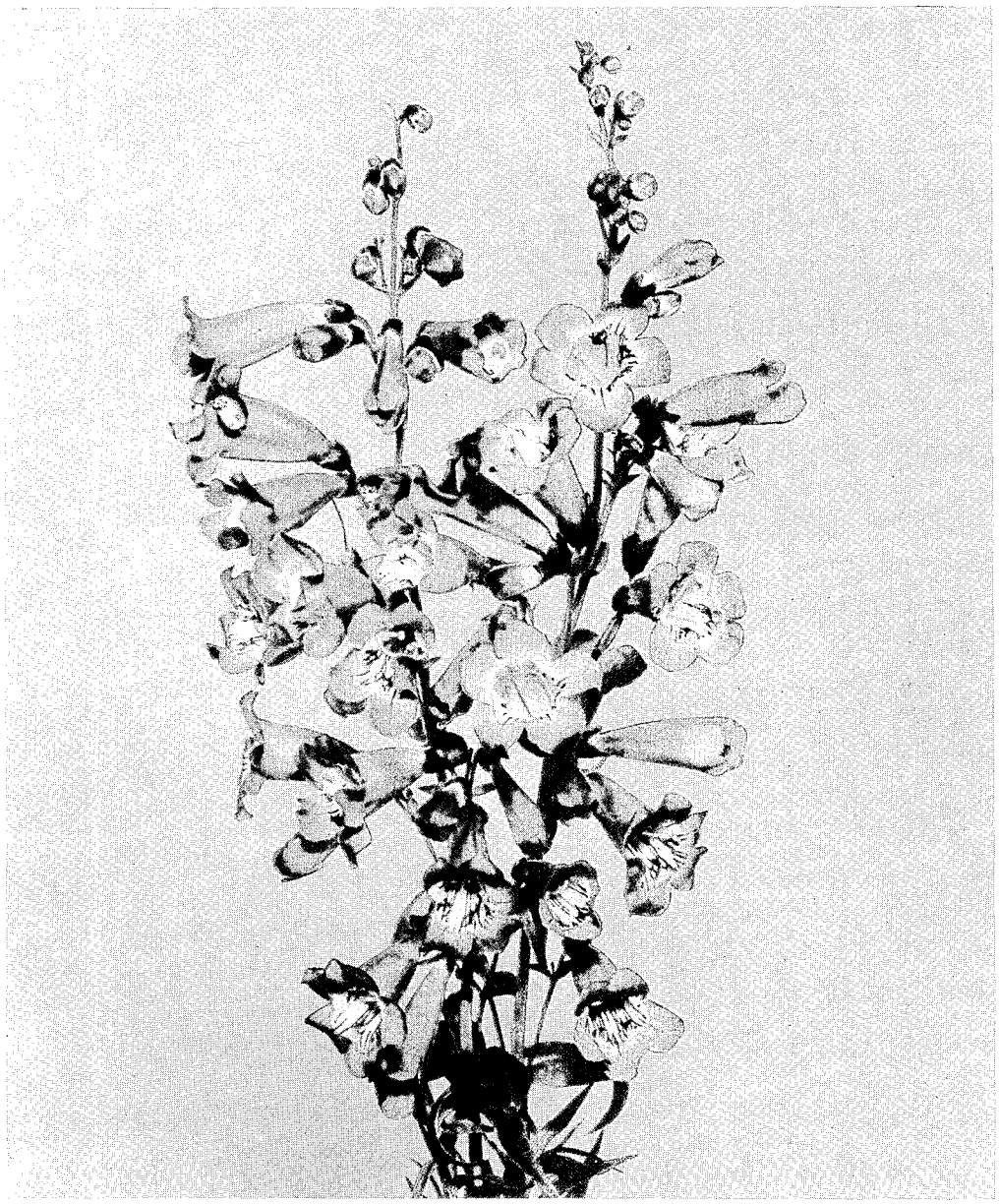
INVENTOR
Clark P. Malmo
By Orville M. Kile
Plant Pat. Agt.

UNITED STATES PATENT OFFICE

744

PENTSTEMON PLANT

Clark P. Malmo, Seattle, Wash.

Application April 8, 1946, Serial No. 660,339

1 Claim. (Cl. 47—60)

My present discovery relates to a new and useful variety of pentstemon plants and is a chance seedling of unknown parentage discovered by me in my gardens in Seattle, Washington.

My new variety possesses many of the characteristics of Giant Ruby and Garnet but has features outstandingly different from these varieties. These differences include larger flowers, more vigorous growth, longer blooming period and different flower color of my new variety. The variety has been asexually reproduced through several seasons and its distinguishing characteristics have proved to be firmly fixed.

The accompanying illustration shows a branch of my new pentstemon variety including some foliage and blossoms in various stages of opening. These are portrayed in as nearly their true colors as it was possible for the artist to make them.

Following is a detailed description of my new variety. Color plate references are to Ridgway's Color Standards and Nomenclature.

*The plant*

Growth: Very vigorous, growing to a height of about 2 feet in this climate and forming large clumps.

Form: Bush; producing 8 or 10 flowering spikes the first year.

Blooming habit: Blooms heavily in early spring and continues throughout the season—a much longer period than most varieties of pentstemon. In this climate where the plant is evergreen, there is a constant show of color.

Cold resistance: Plant survives winters in Seattle and is evergreen. In colder climates it acts as a true perennial and freezes back to the ground each year.

Disease resistance: Very resistant to ordinary diseases of such plants.

Reproduction: Does not reproduce true from seed, but asexual reproduction shows the characteristics to reproduce true.

Foliage:

*Shape.*—Lanceolate with center veins very prominent. No serrations on edge. Flowers arise from axils of leaves which are usually oval pointed.

*Color.*—Jade Green (Plate XXXI) on upper side, Light Cress Green (Pl. XXXI) on under side.

*Aspect.*—Glossy above, smooth and dull below.

*Attachment.*—Leaves attach to stems without stipules.

Stems: Wiry and sturdy. Branching. Flowering stem is approximately Oxblood Red (Plate I).

*The flower*

Bud:

*Size.*—Large, averaging 1½ inches long.

*Form.*—Tubular.

*Sepals.*—Short.

*Peduncle.*—Medium in length.

Bloom:

*Borne.*—Arise from axils of leaves and are borne in clusters or pyramids.

*Size.*—Very large. Trumpets average 2 inches in length.

*Form.*—Trumpet-shaped with five serrations or lobes indicating petal-ends. Of the five stamens, the two shorter ones are pressed against the top of inner surface of trumpet tube.

*Color.*—Outside of trumpet is Spectrum Red (Plate I). Inside of trumpet lobes is Carmine (Plate I) with edges lightening to Spectrum Red (Plate I). The inside of the tube is white marked with lines of Carmine (Plate I). Some of this white extends into the lobes or open part of the trumpet. On the white of the lower lip or lobe there is usually a heavy blotch of Oxblood Red (Plate I), which gives a lively appearance to the whole flower.

Reproductive organs:

*Stamens.*—Five; three extending about to the edge of the white portion of the throat, two slightly shorter ones pressed against the top of the inside surface of the flower. Filaments white, anthers yellow, pollen white.

*Pistils.*—Single and about as long as the longest stamens. Situated in center of trumpet throat. Marguerite Yellow (Plate XXX).

*Comparisons*

The two varieties which my new variety most closely resembles are Garnet and Giant Ruby, but they differ principally as follows:

Compared with Garnet, my new variety is a more vigorous grower, has a much longer blooming season, has much larger flowers and these flowers have a new color combination of lively red with white throat.

Compared with Giant Ruby, my new variety is more hardy, more vigorous, has longer blooming season, better foliage, and larger flowers, the flowers of the new variety being deeper red and with a white throat.

Having thus disclosed my invention, I claim:

The new and distinct variety of pentstemon plant, substantially as shown and described, characterized particularly by its vigorous growth, its hardiness, its long blooming season, its shiny dark foliage, its large flowers, and the new color of its flowers of Spectrum Red with white throat.

CLARK P. MALMO.